US006071005A

United States Patent [19]

Ekambaram et al.

[11] Patent Number: 6,071,005

[45] Date of Patent: Jun. 6, 2000

[54] DISPOSABLE STORAGE, TRANSPORT AND RESUSPENSION SYSTEM

[75] Inventors: Anand Ekambaram, Brookhaven; Wendy L. Radcliff, Souderton; Mark S. Rienstra, Lansdale, all of Pa.; Brett L. Allred, Hyde Park; Doyle W. Stewart, Hyrum, both of Utah

[73] Assignee: Merck & Co., Inc., Rahway, N.J.

[21] Appl. No.: 08/873,095

[22] Filed: Jun. 11, 1997

Related U.S. Application Data

[60] Provisional application No. 60/020,970, Jun. 11, 1996.

[51] Int. Cl.[7] .................... A61B 19/00

[52] U.S. Cl. .................... 366/173.2; 366/167.1; 366/165.1; 604/416; 604/408

[58] Field of Search .................... 366/136, 159.1, 366/167.1, 173.1, 173.2, 191, 349, 165.1; 604/408, 416; 206/219; 383/904

[56] References Cited

U.S. PATENT DOCUMENTS

| | | | |
|---|---|---|---|
| 3,647,397 | 3/1972 | Coleman | 366/167.1 |
| 5,160,333 | 11/1992 | Wells | 604/408 |
| 5,257,983 | 11/1993 | Garyantes et al. | 604/408 |
| 5,304,130 | 4/1994 | Button et al. | 604/416 |
| 5,350,080 | 9/1994 | Brown et al. . | |
| 5,362,642 | 11/1994 | Kern . | |
| 5,385,564 | 1/1995 | Slater et al. | 604/416 |

*Primary Examiner*—Tony G. Soohoo

*Attorney, Agent, or Firm*—Elliott Korsen; Mark R. Daniel

[57] ABSTRACT

The present invention relates to a package for storing, mixing, resuspending and dispensing sterile or non-sterile solutions or suspensions and comprises a sterilizable bag having fittings which provide for the introduction and exit of fluids and solids, as well as means for resuspending and stirring the fluids. Additionally, structural support means are provided for shipment, filling and dispensing. Unlike conventional stainless steel equipment, the system is disposable, does not require cleaning, provides for safe, rapid and accurate resuspension of suspended solids and can accommodate a wide range of liquid volumes.

10 Claims, 4 Drawing Sheets

DISPOSABLE STORAGE, TRANSPORT AND RESUSPENSION SYSTEM

This application claims the priority of provisional application Ser. No. 60/020,970 filed Jun. 11, 1996.

BACKGROUND OF THE INVENTION

The present invention relates to a system for the transport, storage, mixing and resuspension of sterile and non-sterile liquids. In particular, it relates to a system for use with suspensions used in the pharmaceutical industry.

In the chemical industry, and in particular the pharmaceutical industry, there is a need for a system capable of holding liquids and mixtures of liquids and solids where a sterile environment can be maintained while providing means for stirring, mixing, resuspending, sampling and complete delivery of the contents. To date, the industry has relied upon stainless steel storage vessels with associated stirring devices, ports and mixers. These associated pieces of equipment require special seals in order to assure that the sterile conditions established within the device are maintained during mixing and pumping.

Due to the weight of these stainless steel devices, they are difficult to maneuver, which leads to increased production times. These stainless steel systems often require special handling equipment. When these stainless steel devices are used to transport bulk product, significantly higher shipping costs result due to the weight of the container and the added cost of returning the empty system for future use.

Since the stainless steel systems are not disposable, they must be cleaned and resterilized before being reused. This may involve chemical cleaning with agents such as perchlorate solution, and the attendant disposal problems associated with disposal of such products. After cleaning, the systems must be inspected and tested to assure that all foreign matter has been removed. Since new products will be introduced, validation of the cleaning and resterilization procedures as well as tests to assure efficacy must be completed. This also adds to the costs and complication of using the stainless steel systems.

Since the stainless steel systems are expensive, it is not cost effective to maintain several different sizes of the vessels. As a result, vessel size is usually set to the largest expected batch of material. When small batches are prepared, they are stored in oversized containers with the attendant costs and problems which have been previously described.

One of the primary uses for this type of vessel is the storage and transportation of sterile suspensions of alum in an aqueous medium for use in the production of vaccines. In practice, a sterile alum suspension is prepared in the vessel and shipped to the area where inoculation with the bulk virus or bacteria stock will occur. Since the suspension may be prepared well in advance of inoculation, the system must also serve as a storage container.

Prior to inoculation, the alum must often be resuspended. In many instances, uniform particle size and the preparation of a homogeneous suspension of the alum are critical to the success of the final product. Once resuspension has been assured, the suspension may be pumped into a vessel where inoculation will occur or inoculation may be carried out in the storage container.

It is apparent that certain production, shipping and storage problems exist with the current systems.

It is therefore the object of this invention to replace the stainless steel container with a plastic system which is lighter, less expensive, disposable, affords a procedure to resuspend any materials that may settle over time, maintains sterility, and provides a means of obtaining samples of the contents so that uniformity can be assured.

It is a further object to provide a system that can be used where a sterile environment is not necessary.

In order to provide such a system the device must be capable of assuming any needed volume. It must also be capable of being sterilized and maintaining the sterile environment for extended periods of time. Additionally, the surface of the device which comes in contact with the vaccine suspension must not interact with the product. That is, it must not absorb protein, adjuvants or other ingredients from the suspension. Additionally, all fittings and connections to the device must be sterilizable and must be capable of maintaining the sterility of the product during storage.

In order to be practical in an environment including sterile vaccines, the new system must be capable of resuspending alum within a two hour period of time. More conveniently, the resuspension should be possible within 30 minutes.

The product must also be capable of being shipped by regular carrier over great distances or moved by conventional carts inside a manufacturing area.

Since the uniformity of the suspension is critical to the uniformity of the final vaccine product, the device must allow dispensing of product with no apparent settling during the dispensing period. In addition, the system must be designed to deliver as much of the suspension as possible so that only a minimal amount of material is retained within the system once dispensing is complete.

The device of this invention provides for a light weight, sterilizable system capable of mixing, storing, resuspending, shipping and dispensing solutions or suspensions. The instant device of this invention has demonstrated the ability to overcome the problems discussed above and provide reliable, homogeneous suspensions for the manufacture, mixing, storage and dispensing of aqueous suspensions.

SUMMARY OF THE INVENTION

A disposable transport, storage and resuspension system for use in the manufacture of sterile and non-sterile liquids and suspensions is presented comprising a collapsible container and a support device, the collapsible container having means for ingress and egress of fluids and solids into the container and means for mixing and resuspending the contents of the container.

DETAILED DESCRIPTION OF THE INVENTION

There is disclosed a disposable transport, storage and mixing system for use in the manufacture of sterile and non-sterile liquids and suspensions comprising a collapsible container and a support device, the collapsible container having means for ingress and egress of fluids and solids into the container and means for mixing and resuspending the contents of the container.

For the purpose of this invention, a "transport, storage and mixing system" is a device which can be used to hold a volume of liquid or liquid and solid in a manner which is suitable for shipping either locally or over great distances, having the capacity to provide for agitation of the contents. In one preferred embodiment of this invention, the system is configured to provide for the storage, transport and mixing of liquids or liquids and solids which are sterile. In a further preferred embodiment of this invention, the system provides for storage, transport and mixing of a suspension useful in the preparation of a vaccine. In the most preferred embodiment of this invention, the system provides for storage, transport and mixing of an alum suspension that may be inoculated to produce a vaccine.

The following description of this invention is provided to enable any person skilled in the art to make and use the present invention and sets for the best mode contemplated by the inventor for carrying out this invention. Various modifications, however, will remain readily apparent to those skilled in these arts.

While the present invention is described herein in the context of a system for the storage, transportation and mixing of a suspension of alum for use in the production of a vaccine, artisans will understand that the present invention is not so limited. The present invention has equal application to other fluids that require mixing, sterile or non-sterile conditions, portability and ease of disposal.

Figure 1:
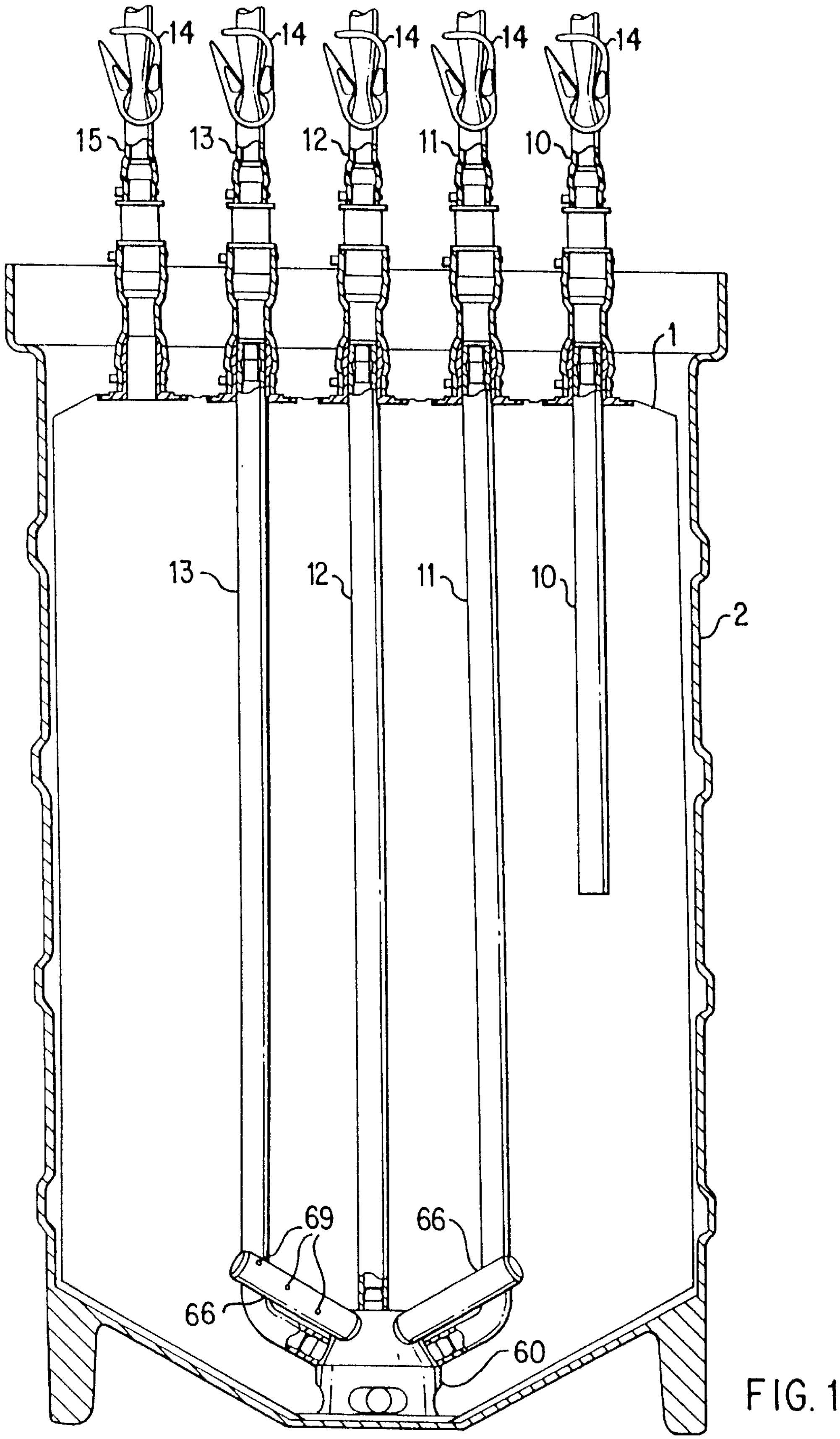
FIG. 1 is a cross section of the preferred embodiment of the system which includes the collapsible container and the support device.

Referring to FIG. 1, a preferred version of the collapsible container (1) and a support device (2) are shown. The collapsible container (1) in the drawing includes means for ingress (15) and egress (13) of fluids and solids into and out of the container and means for mixing and resuspending (10, 11 and 12) the contents of the container.

The collapsible container may be fabricated from any suitable material that will function within the desired temperature range and will not adversely impact the substance to be contained. By "collapsible container" is meant that the container (1) will not support its own weight. Therefore, when the container is empty, it collapses upon itself. Since one of the primary functions of the container is for use in the preparation of alum based vaccines, it is further preferred that the collapsible container be designed to withstand sterilization using Gamma irradiation or other suitable techniques which are known in the art.

In a preferred embodiment of the invention, the collapsible container is initially evacuated of air before being treated with Gamma radiation. The collapsible container may then be shipped in its most compact state and stored in this manner until needed. When a liquid is added to the collapsible container, the container expands as needed in response to the added volume of fluid. As a result of this feature, the head space, or air volume, within the container is held to a minimum.

In a preferred embodiment of this device, a polymeric material, such as linear low density polyethylene is used to produce the collapsible container. This material meets the requirements set forth above in that it will not interact with aqueous solutions or suspensions, does not absorb the media or innoculum used to produce a vaccine and is useful between about 1° C. to about 60° C. Other polymeric materials which meet the requirements of this device may also be used to construct the collapsible container.

In the most preferred embodiment of the collapsible container, the container comprises three layers, the inner most layers comprising blown film polyethylene and the outer layer is a co-extruded EVOH nylon.

The collapsible container (1) has means for ingress (15) and egress (13) of fluids and solids into and out of the container. That is, liquids, suspensions and mixtures of liquids and solids may be added to the collapsible container through inlet means such as tube (15). The chemical integrity and sterility of the collapsible container is assured through the incorporation of valve means such as the hose clamps (14) shown in FIG. 1. Since the collapsible container is initially evacuated before use, when clamp (14) of tube (15) is opened and fluid flows in, the container expands and take the shape of the support device (2) or if a support device is not present, the collapsible container expands to the limits of its own shape.

The support device (2) allows for long distance transport of the container (1). Additionally, the angle of the bottom of the support device is crucial for both the suspension of the alum and for complete draining of the container.

The collapsible container (1) is also equipped with means for mixing and resuspending the contents of the container. This is accomplished in the preferred embodiment of the invention using a short dip tube (10) and a full length dip tube (11) and a return tube (12), which are connected to a mixing block (60) which is fitted with a plurality of mixing arms.

The mixing block may be fabricated from low or high density polyethylene. The tubing connected thereto may be any type of flexible tubing suitable for the operation of the system.

Addition of tubing and various fittings is accomplished using thermal welding. This may be accomplished using a Vertrod Heat Sealing Machine or other suitable device.

Figure 2:
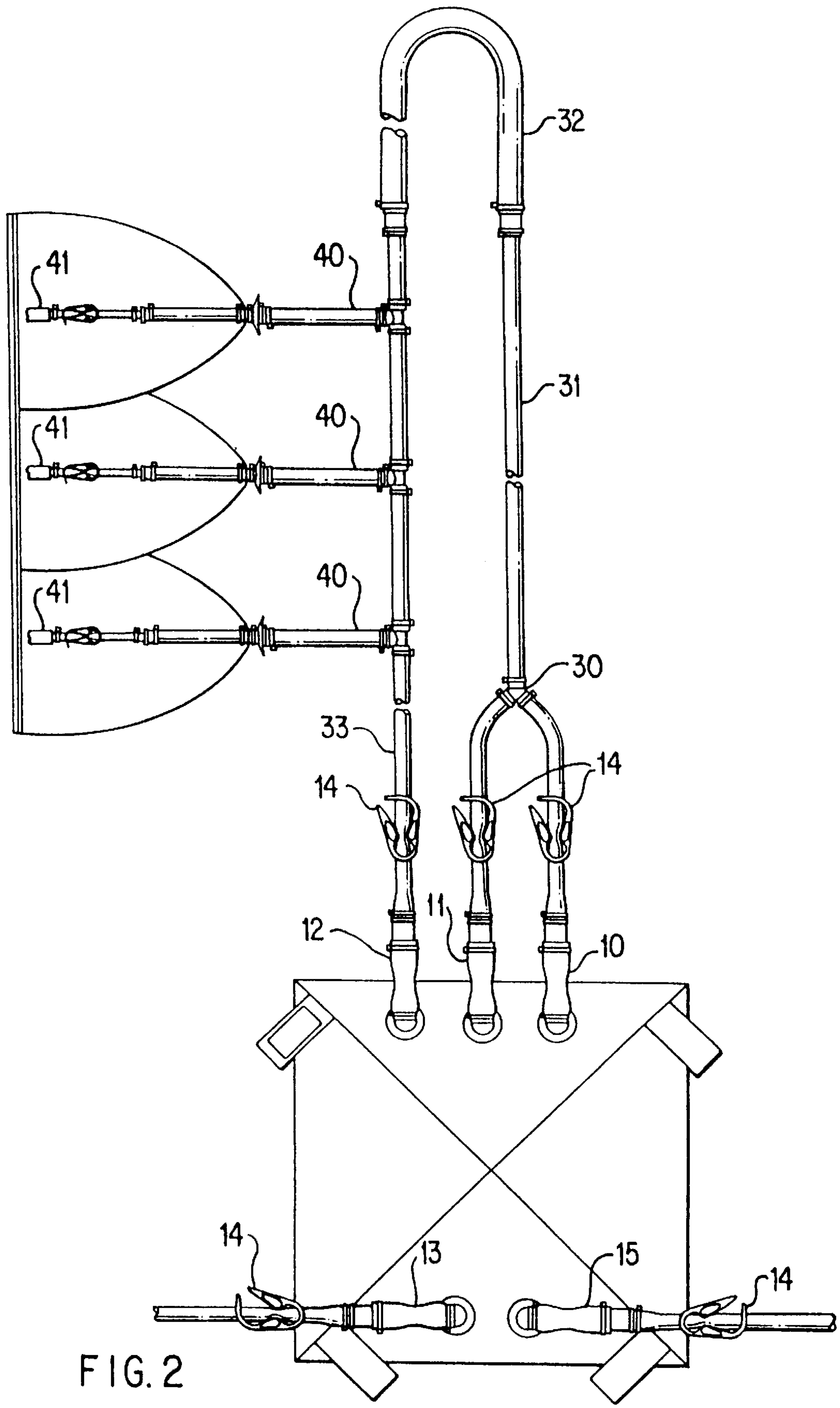
FIG. 2 is a schematic diagram of the enclosed mixing system.

With reference to FIG. 2, the preferred means for mixing and resuspending the contents of the container are shown diagramatically in this view of the preferred device. In this preferred embodiment, material from inside the collapsible container may be withdrawn through the short dip tube (10) or the full length dip tube (11) depending upon the open or closed state of the snapper clamps (14) attached to dip tubes (10) and (11). The material may be withdrawn using, for example a peristaltic pump (32) and returned to the collapsible container through return tube (12). In practice, a piece of tubing is included between the "Y" connector (30) and the pump (32) and a second piece of tubing is included between the pump (32) and return tube (12). This configuration results in a closed loop system for mixing and resuspending the contents of the collapsible container which maintains sterility and assures proper mixing.

Referring again to FIG. 1, the short dip tube (10) may protrude from about 1% to about 80% of the distance from top of the collapsible container to the bottom, when the container is full of liquid. Using this tube, the liquids and solids contained within the collapsible container are drawn from an area above the mixing block (60). Additionally, the full length dip tube (11) may be used to withdraw material from the container. This tube is connected to the mixing block (60) and communicates the inside of the mixing block (60) with the closed loop system.

Figure 3A:
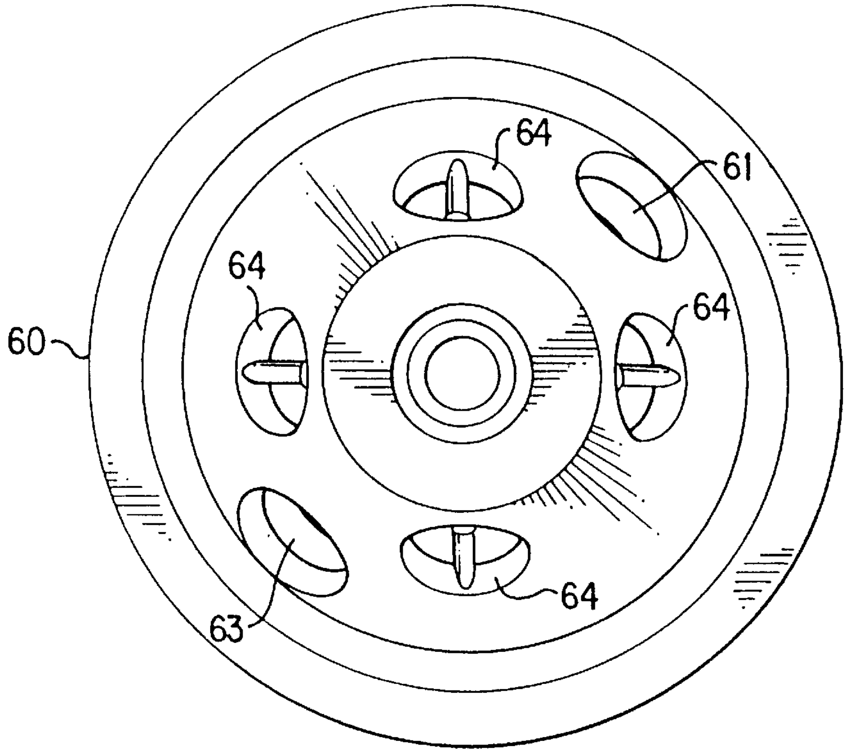
FIGS. 3*a*–3*b* is a top view of the mixing block.
Figure 3B:
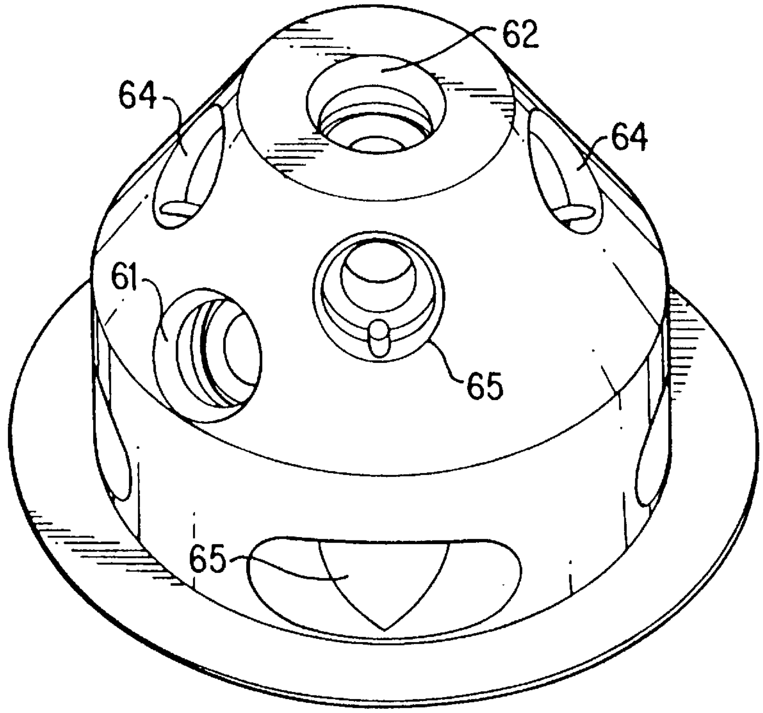

A top view of the mixing block (60) is shown in FIG. 3 *(a)*. This block may be machined from a single piece of suitable plastic, or in the alternative it may be molded either as one piece or as multiple pieces which are then affixed using welding, gluing, mechanical attachment or any other form of attachment known in the art. Port (61) is used to connected the full length dip tube (11) to the mixing block. Port (62) receives the return tube (12). The material which is pumped back through the return tube (12) is diverted in the mixing block and channeled to the spray arms (66) which are shown in FIG. 1, and are attached to the mixing block at ports (64). The contents of the collapsible container may be evacuated through egress tube (13) which is connected to the mixing block (60) at port (63). As indicated in FIG. 3(*b*), the bottom of the mixing block has openings (65) which communicate the inside of the container with the full length dip tube (11). Therefore, when the contents of the container (1) are circulated using full length dip tube (11), mixing from the bottom of the container is assured.

Figure 4:
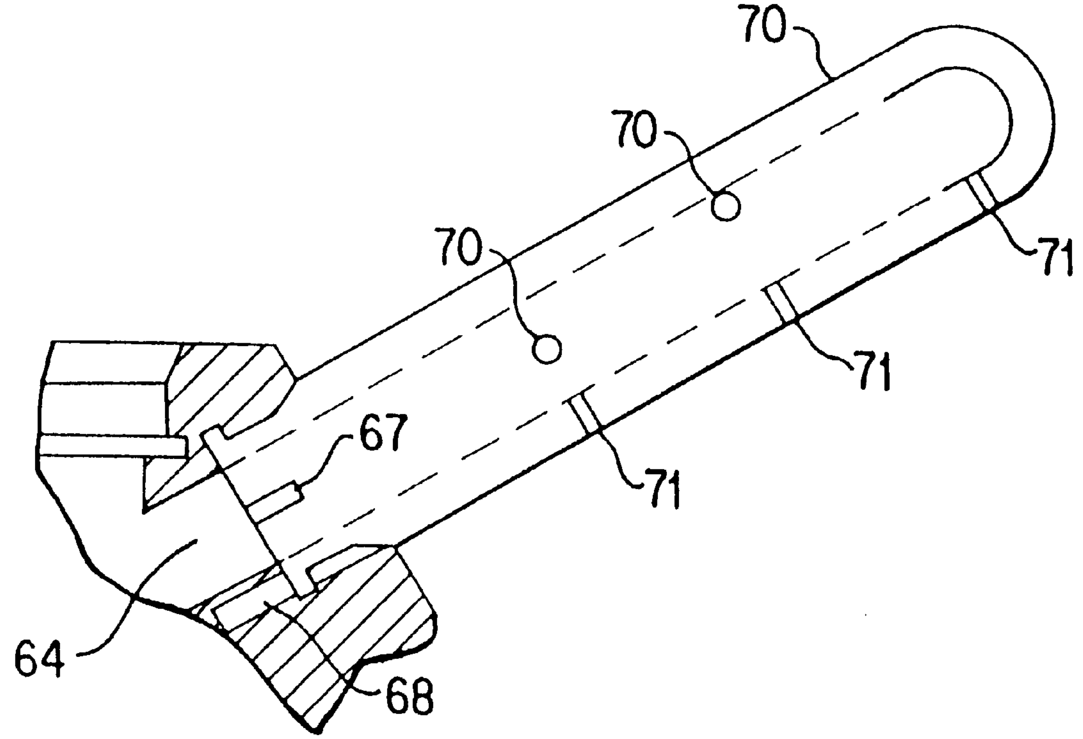
FIG. 4 is a side view of the mixing arms.

A side view of the spray arms is shown in FIG. 4. Each spray arm consists of a hollow tube which is open at the end which fits within port (64) of the mixing block and is closed at the opposite end. Each of the spray arms contains a plurality of apertures which communicate the inside of the collapsible container (1) with the inside of the mixing block (60). In practice, material from within the tank is circulated through the closed loop and pumped back into the mixing block (60) where it is channeled into the spray arms (66) and exits through orifice (70). The position of the various orifices (70) relative to the base of the container is as follows:

The mixing arm has a primary set of holes drilled longitudinally along the bottom of the arm (71) which allows fluid to sweep the region of the container under the arm. A secondary set of holes, useful in mixing and resuspending material within the container, is drilled along the side of the arm. Beginning at a point closest to the block, the first hole is drilled at an angle of 0°. The subsequent holes along the side of the arm are set at increasing angles up to 45°. The fluid exiting from these secondary holes creates a swirling vortex flow pattern that sweeps the side of the barrel and lifts any sediment towards the upper regions of the bag.

In the preferred embodiment, the mixing tubes are positioned within the mixing block (60) using locator rods (68) as shown in FIG. 4. This allows for accurate and reproducible positioning of the orifices during manufacture.

The mixing arms are machined with a set of longitudinal slots (67) in the fitted end. One slot is larger than the others so as to accommodate a locator pin. The main body of the mixing block is machined with holes designed to receive the fitted ends of the arms. The hole design uses a barbed interference fit. The locator pin is inserted into a small pilot hole inside the block. The arms are inserted into the block with the larger slot sliding over the locator pin. The locator pins are situated in the same place on each block to ensure that the arms are properly oriented during manufacture.

The most preferred embodiment of this device is a system for use in the manufacture of vaccines which comprises: a collapsible container and a support device, the collapsible container being flexible and having a top, bottom and sides which enclose a volume of space, the bottom of the container having a mixing block being weldably affixed inside the container, the mixing block having a top, bottom and sides, the mixing block further having a plurality of recirculation outlets; the mixing block having a plurality of openings which communicate the inside of the mixing block to the inside of the container; the sides of the mixing block having a plurality of spray arms, the spray arms being directed from the bottom of the container to the sides and top of the container, the spray arms being hollow and attached to the mixing block, the top end of the spray arms being sealed, the spray arms having a plurality of holes which communicate the inside of the container with the inside of the spray arms; the top of the container having an inlet tube which provides for ingress of fluids and solids into the container, the top of the container further having a long dip tube which extends from outside the top of the container through the top of the container and inside the container where it terminates in the mixing block, the long dip tube being hollow and communicating the inside of the container, at the bottom of the mixing block, with the outside of the container, the portion of the long dip tube which extends outside the top of the container terminating in a "Y" fitting; the top of the container further having a short dip tube which extends from outside the top of the container, through the top of the container and inside the container to a distance from about 1% to about 80% of the length of the container, the portion of the short dip which extends outside the top of the container terminating in the other arm of the "Y" fitting that is connected to the long dip tube; the top of the container further having a recirculating dip tube which extends from outside the top of the container to the mixing block, the portion of the recirculation dip tube which extends outside the top of the container terminating in a valve, such that when the valve is open, the recirculation dip tube communicates the outside of the container with the inside of the inside of the mixing block; an external recirculation loop being attached to the leg of the "Y" fitting connected to the long dip tube and to short dip tube, the recirculation loop having means for pumping the liquid from the short dip tube or the long dip tube, depending upon the positions of the snapper clamps attached to the long and short dip tubes, to the recirculation dip tube, the liquid then moving out the mixing block and through the spray arms; the top of the container further having a pump out tube which extends from outside the top of the container to the mixing block, the portion of the pump out dip tube which extends outside the top of the container terminating in a valve, such that when the valve is open, the pump out dip tube communicates the outside of the container with the inside of the mixing block; the outside of the container having tabs which allow the container to be fastened to the support device; the support device being a rigid frame capable of holding the container in position when in use; wherein, a solution or suspension is introduced into the container through the inlet tube and mixed or resuspended by pumping the contents from the container through the short or long dip tube, through the recirculating loop and back into the container through the recirculating dip tube; the solution or suspension may be pumped out of the container using the pump out tube.

The closed loop mixing feature has been shown to be particularly effective in resuspending alum which has settled from a suspension. In the preferred embodiment of the invention, the pump has a flow capacity of from about 0.5 L/min to about 50 L/min. The most preferred flow velocity is about 20 L/min. In a series of studies, 200 L of an alum suspension was introduced into the collapsible container and allowed to stand. At the end of one week, the resuspension of this material was examined using nephlometric measurements of the suspended alum as a function of mixing time. The pump was operated at 20 L/min and samples were taken after first back flushing the system for a period of 15 minutes. As the results in FIG. 5 indicate, a homogeneous suspension was achieved after mixing for about 30 minutes. In a similar study, shown in FIG. 6, where the suspension was allowed to settle for one month, a homogeneous suspension was again reached in about 30 minutes.

The closed loop mixing system also provides a means for maintaining homogeneity during delivery of the suspension. After resuspending material which had settled, the concentration of alum in μg/ml of the suspension was determined during the emptying of the system. As FIGS. 7 and 8 indicate, suspensions that stood for one week or one month, both maintained homogeneity during the emptying operation.

Since it is often necessary to sample the material within the collapsible container, sampling means, such as removable tubes (40) may be included within the loop. This is shown schematically in FIG. 2. The sampling tubes consists of an elastomeric tubing with a sterile plug in the end. This tubing is connected via a sterile welder to another piece of elastomeric tubing connected to the sampling vessel.

In this disclosure, there is shown and described only the preferred embodiment of the invention, but, as aforementioned, it is to be understood that the invention is capable of changes or modification within the scope of the inventive concept as expressed herein.

What is claimed is:

1. A collapsible container and a support device for use in the manufacture of sterile and non-sterile liquids and suspensions, the collapsible container having means for ingress and egress of fluids and solids into the container, and means for mixing and resuspending the contents of the container; the egress, mixing and resuspending means comprising a closed loop mixing manifold which is external to the container and a mixing block located inside the collapsible container.

2. The container of claim 1 wherein the mixing block comprises a port for a full length dip tube, a port for a return tube, and a plurality of ports for spray arms.

3. The container of claim 1 wherein the spray arm comprises a hollow tube which is closed at one end, the tube having a plurality of holes which communicate the outside of the tube with the hollow interior of the tube, the holes being positioned such that the primary holes are located longitudinally along the bottom of the arm such that when liquid is pumped into the spray arm, fluid sweeps the region of the container under the arm, the secondary holes are drilled along the side of the arm such that liquid moving out of the secondary holes mixes and resuspends material within the container.

4. The container of claim 1 wherein the closed loop mixing manifold comprises a pump capable of pumping sterile liquids and suspensions from the container, through a "Y" fitting, through a return line and back through the mixing block while maintaining the sterility of the liquids and suspensions.

5. The closed loop mixing manifold of claim 4 wherein the pump has a flow velocity of from about 0.5 L/min to about 50 L/min.

6. The closed loop mixing manifold of claim 5 wherein the pump has a flow velocity of from about 20 L/min.

7. The closed loop mixing manifold of claim 4 wherein a valve and removable tube are weldably attached to the return line such that when the valve is opened, liquid or suspension flowing throughout the manifold enter the removable tube and when the valve is closed the removable tube may be disconnected from the manifold and the material stored within the tube retained for further analysis.

8. A system for use in the manufacture of vaccines comprising:

a collapsible container and a support device, the collapsible container being flexible and having a top, bottom and sides which enclose a volume of space, the bottom of the container having a mixing block being weldably affixed inside the container, the mixing block having a top, bottom and sides, the mixing block further having a plurality of recirculation outlets;

the mixing block also having a plurality of openings which communicate the inside of the mixing block to the inside of the container; the sides of the mixing block having a plurality of spray arms, the spray arms being directed from the bottom of the container to the sides and top of the container, the spray arms being hollow and attached to the mixing block, the top end of the spray arms being sealed, the spray arms having a plurality of holes which communicate the inside of the container with the inside of the spray arms;

the top of the container having an inlet tube which provides for ingress of fluids and solids into the container, the top of the container further having a long dip tube which extends from outside the top of the container through the top of the container and inside the container where it terminates in the mixing block, the long dip tube being hollow and communicating the inside of the container, at the bottom of the mixing block, with the outside of the container, the portion of the long dip tube which extends outside the top of the container being fitted with a pinch clamp and terminating on one arm of a "Y" fitting;

the top of the container further having a short dip tube which extends from outside the top of the container, through the top of the container and inside the container to a distance from about 1% to about 80% of the length of the container, the portion of the short dip which extends outside the top of the container being fitted with a pinch clamp and terminating on one arm of a "Y" fitting;

the top of the container further having a recirculating dip tube which extends from outside the top of the container to the mixing block, the portion of the recirculation dip tube which extends outside the top of the container terminating in a valve, such that when the valve is open, the recirculation dip tube communicates the outside of the container with the inside of the inside of the mixing block;

an external recirculation loop being attached to the leg of the "Y" fitting connected to the long dip tube and to the short dip tube, the recirculation loop having means for pumping the liquid from the short dip tube or the long dip tube, depending upon the position of the snapper clamps attached to the long and short dip tubes, to the recirculation dip tube, the liquid then moving out the mixing block and through the spray arms;

the top of the container further having a pump out tube which extends from outside the top of the container to the mixing block, the portion of the pump out dip tube which extends outside the top of the container terminating in a valve, such that when the valve is open, the pump out dip tube communicates the outside of the container with the inside of the mixing block; the outside of the container having tabs which allow the container to be fastened to the support device;

the support device being a rigid frame capable of holding the container in position when in use;

wherein, a solution or suspension is introduced into the container through the inlet tube and mixed or resuspended by pumping the contents from the container through the short or long dip tube, through the recirculating loop and back into the container through the recirculating dip tube; the solution or suspension may be pumped out of the container using the pump out tube.

9. A system for use in the manufacture of sterile and non-sterile liquids and suspensions comprising a collapsible container and a support device, the collapsible container having means for ingress and egress of fluids and solids into the container, and means for mixing and resuspending the contents of the container, said container comprising a flexible plastic container having a top, bottom and sides which enclose a volume of space, the bottom of said container having a mixing block being weldably affixed inside said container.

10. The system of claim 9 wherein the inside of the collapsible container may be sterilized using Gamma irradiation.

* * * * *